United States Patent [19]

Huang et al.

[11] 4,056,638

[45] Nov. 1, 1977

[54] DIELECTRIC DRYING OF FUNGAL MATERIAL AND RESULTANT TEXTURED PRODUCT

[75] Inventors: Hua-Feng Huang, Mendenhall, Pa.; Richard Alan Yates, Wilmington, Del.

[73] Assignee: E. I. Du Pont de Nemours and Company, Wilmington, Del.

[21] Appl. No.: 683,926

[22] Filed: May 6, 1976

Related U.S. Application Data

[63] Continuation-in-part of Ser. No. 587,149, June 16, 1975, abandoned.

[51] Int. Cl.$^2$ .............................. A23J 3/00; A23J 1/18
[52] U.S. Cl. .................................... 426/244; 426/656; 426/802
[58] Field of Search .............................. 260/112, 123.5; 195/28 N, 81; 426/61, 104, 241, 242, 244, 247, 445, 60, 447–448, 636, 516, 517, 802

[56] References Cited

U.S. PATENT DOCUMENTS

| | | | |
|---|---|---|---|
| 3,249,446 | /0000 | Tooby | 426/244 X |
| 3,662,673 | 5/1972 | Boyer et al. | 426/241 |
| 3,784,536 | 1/1974 | Akin et al. | 260/112 R |
| 3,809,614 | 5/1974 | Forss et al. | 426/60 |
| 3,870,805 | 3/1975 | Hayes et al. | 426/516 X |

FOREIGN PATENT DOCUMENTS

1,346,062   1974   United Kingdom.

*Primary Examiner*—Joseph M. Golian
*Assistant Examiner*—R.B. Penland

[57] ABSTRACT

A proteinaceous mass of fungal mycelial fibers is treated by rapid dielectric heating to reduce the moisture content by from 8 to 40 weight percent to give a product with a solids level of 30 to 70 weight percent, and preferably a solids level of 40 to 60 weight percent. The initial proteinaceous mass may be pretreated such as by aqueous thermal shock to reduce the nucleic acid content, before it is formed into fiber bundles of from 0.2 to 1.0 mm. in diameter, and having an average length to diameter ratio of greater than 20. These bundles are interconnected by groups of hyphae or by single hyphal with average diameter of from 0.004 to 0.01 mm. and length to diameter ratio of from 10 to 1000. The dielectric heating process puffs and crosslinks (heat sets) the product which then may be further dried such as in a hot air oven to reduce the moisture content of the mass to the desired level below 10 weight percent. The product is rehydratable to 1 to 5 and preferably 1.5 to 3.0 times its dry weight to yield a form having a texture and chewability resembling meat.

30 Claims, 5 Drawing Figures

DIELECTRIC DRYING OF FUNGAL MATERIAL AND RESULTANT TEXTURED PRODUCT

CROSS-REFERENCE TO RELATED APPLICATION

This application is a continuation-in-part of Ser. No. 587,149 filed June 16, 1975, now abandoned.

BACKGROUND OF THE INVENTION

The present invention relates to edible protein products derived from fibrous fungal material obtained from a fermenter. When such a material is mechanically worked and then directly air dried, it becomes very hard and toughtextured. Similarly, products made from the material by reduction of nucleic acid content and direct air drying of the filter cake also have an undesirable texture.

The use of dielectric heating in the production of edible proteinaceous materials made from substances such as soy flour/soy protein isolate is disclosed in U.S. Pat. Nos. 3,622,673 and 3,810,764.

SUMMARY OF THE INVENTION

The present invention relates to a heat treatment and drying process and resultant product. More specifically, the process involves a rapid heat treatment and partial drying of a fibrous fungal mass using dielectric heating to puff and heat-set the material which generally is followed by a slow final drying such as by hot air. Preferably the fibrous mass is mechanically worked prior to the dielectric heat treatment. The process can produce a range of products which closely resemble various meats in texture.

DETAILED DESCRIPTION

Figure 1:
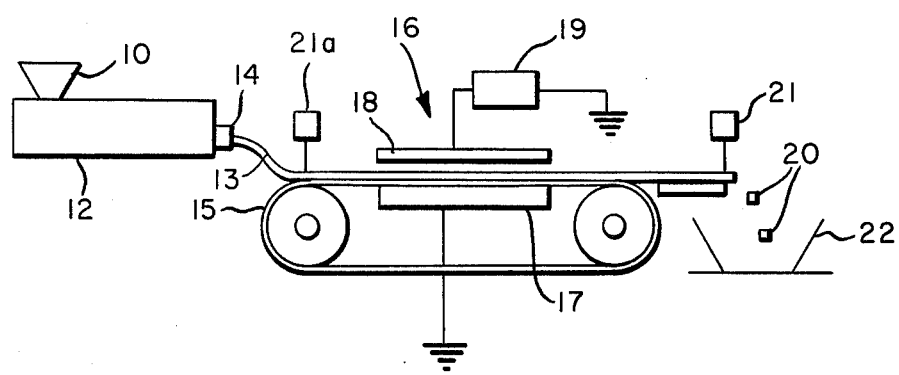
FIG. 1 is a schematic drawing of the extrusion, dielectric drying and cutting apparatus used to perform the process of the present invention.
Figure 2:
FIG. 2 to 5 are photomicrographs of the product of the present invention.
Figure 3:
Figure 4:
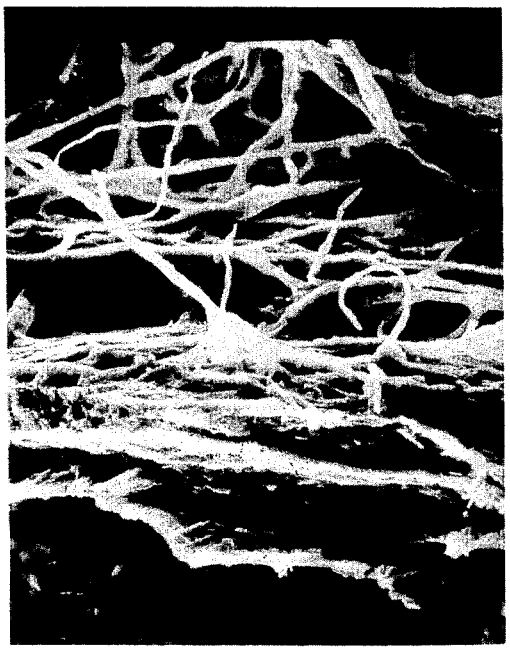
Figure 5:

The starting material for use in the present invention is generally prepared by fermentation of a nontoxic microfungus on an assimilable carbohydrate. The resultant product has a substantial protein content and is useful as food for both humans and animals. Various microfungi may be used to prepare the starting material. The preferred microfungus is *Fusarium graminearum* Schwabe deposited with the Commonwealth Mycological Institute and assigned the number I.M.I. 145,425. Suitable variants of this microfungus also deposited with the Commonwealth Mycological Institute include I.M.I. 154,209; I.M.I. 154,210; I.M.I. 154,211; I.M.I. 154,212 and 154,213. Other suitable nontoxic microfungi include, but are not limited to, *Fusarium oxysporum* (I.M.I. 154,214), *Fusarium solani* (I.M.I. 154,217), and *Penicillium notatum chrysogenum* (I.M.I. 142,383; I.M.I. 142,384; I.M.I. 142,385, I.M.I. 142,386), with the identifying numbers of strains thereof which have been deposited with the Commonwealth Mycological Institute given in parenthesis. A typical preparation of the starting material is as follows:

A continuous 8-liter fermenter is sterilized and continuously charged with a sterile medium consisting of

| | g/per 100 liters |
|---|---|
| $MgSO_4$ | 40.5 |
| $ZnSO_4 \cdot 7H_2O$ | 0.83 |
| $CuSO_4 \cdot 5H_2O$ | 0.167 |
| $MnSO_4 \cdot 1H_2O$ | 0.63 |
| $FeSO_4 \cdot 7H_2O$ | 0.83 |
| $K_2SO_4$ | 10.0 |
| $(NH_4)_2SO_4$ | 144.0 |
| $NaMoO_4 \cdot 2H_2O$ | 0.083 |
| $CoCl_2 \cdot 6H_2$ | 0.17 |
| NaCl | 10 |
| $CaCl_2$ | 8.0 |
| $KH_2PO_4$ | 379.0 |
| Biotin | .0006 |
| Dextrose . $H_2O$ | 8,000.0 |
| Ammonium citrate | 4.0 |
| Water | to 100 liters |
| Boric acid | 0.05 |

The rate of charging the sterile medium is 1.18 liters per hour. The medium in the fermenter is initially inoculated with a spore suspension of the desired organism such as *Fusarium graminearum* Schwabe I.M.I. 145,425 and then stirred with a 6-bladed disc turbine operated at 850 rpm. Air is flowed through the fermenter at a rate of 3.6 liters per minute. Additional oxygen flow is 2.0 liters per minute. The fermenter temperature is 29.2° C., and the pH is 4.8. Ammonia is added to control the pH. The fermenter productivity is 5.45 grams per liter hour. The product, fungal mycelium, is continuously drawn off from the fermenter and collected in a product receiver and held at 8° C. After 185 hours of operation, the pooled product, which was collected and cooled during the final 10 hour period, is then harvested and filtered. The resultant filter cake is then suspended in 8.0 liters of filtrate which has already been preheated to 72° C and adjusted to pH 6.0 with NaOH. Addition of the cake to the slurry decreases the slurry temperature to 64° C which is then maintained for 20 minutes. This treatment serves to reduce the nucleic acid content of the filter cake so that higher levels of ingestion of the material by humans will be permissible, but is unnecessary if the product is to be fed to animals such as ruminants. The slurry is then filtered and washed on the filter bed with one-half the bed volume of distilled water. The filter cake is next dewatered with a vacuum to a solids content of 27.6 weight percent. At this point the wet filter cake comprises an entangled mass of limp flexible mycelial filaments. It is an open network with strands in random orientation except in regions where they have been drawn into some order by mechanical work. Since the strands are flexible, interfilament contacts are frequent and involve relatively large areas of surface contact. If mechanical work is done on the filter cake in a directed fashion, the filaments become ordered in direction by sliding over each other while the area of weak inter-filament contacts increases. The rapid heat setting of these contacts serves to increase the strength of the product even after rehydration so that a marked increase in cookability and chewability of the product is observed.

DESCRIPTION OF THE DRAWING

Referring now to FIG. 1, the filter cake of mycelium is fed to feed hopper 10 of meat grinder 12. Meat grinder 12 is fitted with a screw auger which forces the mycelial mass through die 14 to form an extruded mycelial mass 13 onto conveyor 15. Generally the die of the meat grinder will be fitted with a foraminous member such as a mesh which serves to orient the mycelia within the mass in the machine direction followed by a compaction zone which serves to press the mycelia into contact with each other. Conveyor 15 transports the extruded mycelial mass 13 through dielectric heater 16. Dielectric heater 16 consists of a grounded electrode plate 17, and electrode plate 18 which is activated by radio frequency generator 19. After passing through dielectric heater 16, the mycelia are cut into chunks 20 by knife 21 which alternately may be placed as shown at 21a. The chunks 20 are collected in vessel 22.

The mycelium in the filter cake contain substantial amounts of water. Generally the filter cake will contain from 15 to 40 weight percent solids with a more usual range of from 20 to 33 weight percent solids. The weight percent solids as used herein is determined by weighing a sample, drying the material for 16 hours at 60° C in a vented oven to completely dry the material, and then weighing the resulting dried sample.

The dielectric heating step will generally rapidly dry the filter cake to increase the solids content thereof by from 8 to 40 weight percent as based on the total original filter cake composition to contain from 30 to 70 weight percent solids with from 40 to 60 weight percent solids being the preferred range. It has been found that when the RNA reduced product is dried rapidly to less than 40 and especially less than 30 weight percent solids, the final dried product upon rehydration is tough textured and undesirably hard. It has also been observed that when the RNA reduced product is dielectrically dried rapidly to greater than 60 weight percent solids, and especially when dried dielectrically rapidly to greater than 70 weight percent solids, the ultimate rehydrated product exhibits poor chewability and poor integrity and on rehydration and cooking is soft in texture. Furthermore it is difficult to avoid burning and degradation of the protein when the material is rapidly dielectrically dried beyond 70 weight percent solids. Thus the unexpected result has been found that when dried dielectrically rapidly to within this preferred range of from 40-60 weight percent solids, and then further dried at a much slower rate by conventional means such as hot air, the dried RNA reduced product can be rehydrated to absorb from 1 to 5 and preferably 1.5 to 3.0 times its weight of water. For when the untreated filter cake is dried entirely by hot air, the dried product will only take up about 0.2 to 0.5 times the solids weight of water on rehydration. Further when the product is dielectrically dried rapidly in excess of that provided by the present invention the rehydrated product does not retain its shape and its texture well on cooking.

Although puffing is normally associated with a large expansion in the overall dimensions of the product during the heating step, in this case, puffing refers to the resistance of the material during heating to the shrivelling up or collapse and hardening which take place on slow drying. The rapid heating can expand the product but any excessive expansion of the overall dimensions of the product is generally undesirable since it results in a product which on rehydration has an apparent density less than meat and a texture, strength, and other physical characteristics unlike meat. Thus, expansion of the material is generally needed only when producing a mince type product. Generally the product will not change more than about 20% in volume during the rapid drying step. The rapid drying apparently serves to heatset the product. The heat-setting then evidently serves to cause the cells to retain their physical dimensions and resist further shrinkage. The apparent bulk density of slowly air dried fungal material grown as described above is about 0.85 to 0.95 g/cc, whereas the apparent bulk density of the same material dried in accordance with the present invention generally is from 0.52 to 0.73 g/cc (both cases dried to essential dryness). Thus the puffing heat-setting step serves to retain pores and to cross-link the material so that it can be easily rehydrated. The pore size between the relatively coarse fibers of the product can be controlled by varying the rate of dielectric drying. Generally from 2 to 13 kilowatt (kW)-seconds, kilojoules (kJ), of dielectric energy per gram of solids in the filter cake is used with about 2 to 9 kW-seconds (kJ) per gram being preferred. In order to achieve the proper pore size, this amount of energy should be applied for 5 to 300 seconds covering cross-sectional dimensions of $\frac{1}{8}$ inch (0.32 cm) diameters to $1\frac{1}{2}$ inch (3.81 cm) by $2\frac{1}{2}$ inch (6.35 cm). Larger sizes take correspondingly longer. For instance, a $5\frac{1}{2} \times 5\frac{1}{2} \times 3$ inch (14 × 14 × 7.6 cm) thick chunk takes about 20 minutes. To achieve 3 kW-seconds per gram in 120 seconds, 25 watts per gram are needed to be applied to the material. Watt per gram value can be calculated by dividing the energy input in Watt-seconds per gram with the heating time in seconds. We have found that for a mince-type product the energy is applied for 5 to 60 seconds with about 15 seconds being the optimum, whereas for a $\frac{1}{2} \times \frac{1}{2}$ inch (1.27 cm by 1.27 cm) chunk-type product the energy should be applied for 30 to 180 seconds to reach the 30 to 70 weight percent solids level with the optimum being about 130 seconds. For $1\frac{1}{2} \times 2\frac{1}{2}$ inch (3.8 × 6.4 cm) ribbons about 200 to 300 seconds are used with 250 seconds being optimum. The dielectric heating is generally performed at a frequency of from 1 to 3,000 Megahertz. Higher frequencies than 3,000 MHz can be used but are more expensive to produce and control and do not appear to offer any advantage. Frequencies about 13 to 90 MHz are preferred for ease of control, product uniformity, lower cost per kilowatt, equipment life, etc. However, frequencies into the microwave range can be used. In particular 915 and 2450 MHz frequencies have been used satisfactorily.

The dewatered filter cake may be mechanically worked prior to the dielectric heating. When this is done, it is generally preferred that the high frequency electric field of the dielectric heater be applied at right angles to the orientation of the fibers developed in mechanically working the material being treated. It has been discovered that the direction in which the high frequency electric field is applied has a significant influence on the structure of the finished product, and the best chewability in the final rehydrated product is obtained when the electric field is applied at right angles to the direction of the fibers. Thus a vertical field is preferred for continuous strip production. However, when the voltage across the air gap is large it may be desirable to use a disperse field.

In order for the water vapor created by the dielectric heating to expand and heat-set the product properly, the thickness of the material being dried should be between 0.2 to 15.0 cm. Below this thickness the water vapor can escape without adequate puffing and heat-setting of the product and the pore size is difficult to control. When heating material greater than 15.0 cm in thickness, it is difficult to control voids in the product which are undesirable for some end uses. For products of about 1.25 by 1.25 cm cross-sections, void formation can be minimized by feeding continuous lengths of product through the dielectric oven and using 130 to 180 second drying times to partially dry and heat-set the product (up to 300 seconds for larger cross sections).

If desired, minor amounts of a binder such as gluten may be incorporated in the material prior to drying. In certain instances it is desirable to dry the material in a steam atmosphere in order to avoid skin formation on the product.

The dielectric heating step also reduces the odor of the product as compared with that of the product obtained by hot air drying only.

The dielectrically heat-set and partially dried material can be frozen wet. When thawed, and optionally rehydrated, it retains its puffed heat-set structure, improved cookability, chewability, etc.

After the rapid dielectric heating step, the product is further dried to a moisture content of less than 10 weight percent in order to improve the shelf life and texture of the product. Generally this step is carried out at from 50° C to 150° C. At 50° C adequate drying generally takes about 20 hours. At 150° C adequate drying generally takes about 20 minutes.

After drying, the fungal product is stored until it is formulated into a food product. Upon formulation, the dried fungal product is rehydrated with water. The preferred products of the present invention will take up from 1 to 5 times their weight (as based on the actual solids content thereof prior to rehydration) of water. The rehydration measurement is made by immersing the dried product in boiling water at standard atmospheric pressure for 20 minutes followed by draining and blotting with paper towels.

The mechanical working step is not essential and, if desired, may be omitted for some end uses in order to provide a bread-like product that may be used as a ground meat extender. However, in the preferred aspect of the invention, it is desired to produce a chunky product which resembles meat in texture after cooking, and therefore, it is necessary to perform some mechanical working on the product prior to the dielectric heating step. In order for the best results to be obtained in a texturized product, the fungal hyphae should have their turgor reduced. The original cells as grown are relatively rigid and when mechanically worked they tend to dewater and due to their rigidity the resultant product has an undesirably few number of contact points between individual hyphae resulting in poor mechanical strength. The nucleic acid reduction step described above in the description of growing the fungal fibers adequately reduces the turgor of the fibers for this purpose. Alternatively the fibers may be washed with a dilute salt solution to remove water from within the cells thereby reducing the turgor of the hyphae. The mechanical working serves to align the hyphae and to press them together to form larger fibers or fiber bundles made up of many hyphae. The larger fibers are interconnected by many hyphae giving a meat-like texture to the product. To prepare a mince-type product, the filter cake which preferably contains 20–33 weight percent solids is extruded through a plate about ¼ inch (0.64 cm) thick provided with holes from ⅛ inch (0.32 cm) to 7/16 inch (1.11 cm) in diameter, with about 3/16 inch (0.48 cm) being optimum, to form strands which are then dried by dielectrical heating for 5 to 60 seconds to a 30 to 70 weight percent solids level. The material may be cut, ground, or chopped into lengths of ⅛ inch (0.32 cm) to 7/16 inch (1.11 cm) with about ¼ inch (0.64 cm) being preferred either before or after the final drying. The dielectric heating in this case causes some expansion and puffing as well as heat-setting of the product. The product is then further dried to below 10 weight percent moisture over a period of 20 minutes to 20 hours to improve texture and the shelf life thereof.

Another type of product which can be produced by the process of the present invention closely simulates a porkloin slice. This is prepared by extruding the filter cake as described in the example below to form a 1.27 cm square strip. The strip is then cut into lengths of about 1 to 1½ feet (30.48 to 45.72 cm). The lengths are then bundled up with about 6 to 15 strips to a bundle. The bundle is wrapped with cheese cloth or plastic film and then hand worked using a motion similar to that used to milk a cow to extend the length of the bundle 1.5 to 3 times with about 2 times being preferred. The resulting extended bundle is then sliced at ½ inch (1.27 cm) intervals giving a ½ inch (1.27 cm) slice with a ¼ inch (0.64 cm) to ¾ inch (1.90 cm) slice being typical. Using the dielectric apparatus described in the example below with its electrode in a disperse field configuration and one slice in the oven at a time, an 88 second residence time and the distance between the plane of upper electrode tips and the plane of the lower electrode tips of 1⅜ inch (3.49 cm) results in a product containing 40 weight percent solids. Production rate can be increased by simultaneously processing a higher number of slices equally spaced along the belt as long as the rated power of the dielectric heater is not exceeded. Alternately, applicants have used a 2450 MHz multimode cavity oven to heat four slices at a time. Using a power setting of 1 kilowatt and 150 seconds residence time, the resultant product contained 50 weight percent solids. The pork loin slice is further dried to below 10 weight percent moisture over a period of 20 minutes to 20 hours to improve the shelf life thereof.

The preferred product to which the process of the present invention is applicable is chunks as described in the example below. The extrusion process described therein is not a part of the present invention. However, the heat setting and drying of the extruded product so as to retain its texturized structure, yet providing a dried rehydratable product is part of this invention.

DESCRIPTION OF THE PREFERRED EMBODIMENTS

EXAMPLE 1

A filter cake of mycelium prepared from *Fusarium graminearum* Schwabe I.M.I. 145,425, prepared as described above, is fed into a small electrically driven meat grinder. The filter cake contains 27.6 weight percent solids. The filter cake is extruded through a 5 cm diameter die fitted with a 0.6 mm square mesh screen and then through a 4 to 1 compaction die at a rate of 2.5 feet per minute (76 cm per minute) onto a Teflon ® (synthetic fluorocarbon polymer manufactured by E. I. duPont de Nemours and Co.) coated mesh conveyor belt 3 inch (7.6 cm) wide driven at 2.5 feet (76 cm) per minute. The belt is passed between two flat rectangular dielectric heater electrodes 15 inch (38 cm) wide by 18 inch (45.7 cm) long, by ¼ inch (0.63 cm) thick. The electrodes are spaced 2⅜ inches (6 cm) apart. A ½ inch (1.27 cm) thick Teflon ® belt guide 3½ inches (8.9 cm) wide is set on the lower electrode, which electrode is grounded. The conveyor belt is in contact with the top of this belt guide. The presence of this belt guide serves to position the product in the field such that the heating intensity tends to be uniform throughout the product cross-section. This eliminates a tendency of the product to over puff at the bottom and under puff at the top. The upper electrode which is covered with ⅛ inch (0.32 cm) thick Teflon ® sheet is connected to an 85 MHz tuneable 8 kilowatt adjustable radio frequency generator unit manufactured by W. T. La Rose Associates of Cahoes, N.Y. This unit is tuned to 85 MHz and is operated at a power output up to 8 kilowatts. The product coming off the dielectric heater contains 50.7 weight percent solids and is cut into ½ inch to 1 inch (1.27 cm to 2.54 cm) length chunks. The chunks are then collected and dried in an air oven at 50° C for 20 hours to achieve a moisture content of less than 1 weight percent. On boiling in water for 15 minutes at atmospheric pressure the chunks take up 1.8 times their dry weight of water.

Photomicrographs showing a freeze fractured product chunk magnified 60×, 100×, 300×, and 1,000× are presented as FIGS. 2, 3, 4 and 5 respectively. It will be noted that the product is made up of relatively coarse fibers having an average diameter of about 0.5 mm and a length to diameter ratio of greater than 20. These fibers have been found to vary from 0.2 to 1.0 mm in diameter in the various meat-like products Applicants have prepared, and are interconnected with hyphae which have an average diameter of about 0.008 mm and an average length to diameter ratio of about 100. Generally, these hyphae in the various meat-like products applicants have prepared, have been found to vary from 0.004 to 0.01 mm in diameter and to have length to diameter ratios of from 10 to 1,000. In addition, the fibers have been found to be connected by at least one hypha in each 0.1 to 1.0 mm of each fiber length.

The product shown in FIGS. 2-5 contains about 55 weight percent protein. Generally the product will contain from 45 to 60 weight percent protein.

EXAMPLE 2

A filter cake containing 34 weight percent solids is extruded into a 1.27 cm by 1.27 cm cross-section rope using the die described in Example 1 at a rate of 4.6 feet per minute (140 cm per minute) onto a Teflon ® coated mesh conveyor belt 3 inches (7.5 cm) wide driven at 4.6 feet (140 cm) per minute. The belt is passed between two sets of electrode arrays (1.9 cm diameter aluminum rods spaced 20.3 cm apart in each set) of 32 inches effective heater length in a dispersed field configuration. The distance between the plane of the upper electrode tips and the plane of the lower electrode tips is 3.75 inches (9.5 cm). The conveying belt is positioned 1.125 inches (2.86 cm) above the plane of the lower electrode tips so that the heating intensity tends to be uniform throughout the product cross-section. The lower electrode is connected to a 27 MHz tunable 6 kilowatt adjustable radio frequency generator unit manufactured by Fitchburg Industrial Products Company of Fitchburg, Massachusetts. This unit is tuned to 27.5 MHz and is operated at a power output to extrudate of 4.7 kilowatts. The product coming off the dielectric heater is cut into ½ inch (1.27 cm) to 1 inch (2.54 cm) length chunks. The chunks contain 47.4 weight percent solids. The chunks are then collected and dried in an air oven at 50° C for 20 hours. This dried product has a moisture content of less than 1 weight percent. On boiling in water for 20 minutes at atmospheric pressure and blotting with paper towels, pieces of this dried product take up 1.5 times their dry weight of water.

EXAMPLE 3

A filter cake of mycelium of *Fusarium graminearum* Schwabe I.M.I. 145,425, prepared as described above, is fed to a hydraulic ram type extruder. The filter cake containing 30 weight percent solids is forced through an oval die measuring 3.8 cm by 6.35 cm fitted with a 0.6 mm mesh screen over a 19 strand breaker plate. There is a 4 to 1 reduction in filter cake size as the material passes from the screen through the breaker plate and a further 1.3 to 1 reduction in filter cake size as the merged strands pass from the 19 strand breaker plate to the oval die outlet. The extrudate is discharged through the oval die at a rate of 414 cm per minute onto a conveyor belt. The extrudate is cut to 150 cm lengths, which are removed from the conveyor belt and placed on trays. After a brief time the 150 cm lengths are individually placed on a Teflon ® coated mesh conveyor belt 7.5 cm wide driven at 24 cm per minute. The belt is passed through two flat rectangular dielectric heater electrodes 38 cm wide by 72 cm long, by 0.63 cm thick. This provides for a residence time of 180 seconds in the dielectric heater. The electrodes are spaced 15.5 cm apart. A 1.25 cm thick Teflon ® belt guide 8.9 cm wide is set on the lower electrode, which electrode is grounded. The conveyor belt is in contact with the top of the belt guide. The presence of the belt guide serves to position the product in the field such that the heating intensity tends to be uniform throughout the product cross-section. The upper electrode which is covered with a 0.32 cm thick Teflon ® sheet is connected to an 85 MHz tuneable 12.5 kW adjustable radio frequency generator unit manufactured by W. T. La Rose Associates of Cahoes, N.Y. This unit is operated at a power output of 5.4 kilowatts to the extrudate. The product coming off the dielectric heater contains 40.3% solids. The product is further broken into chunks of 1.9 cm × 1.9 cm × 2.5 cm and dried in an air oven at 90° C for 4 hours. This dried product has a moisture content of less than 1 percent. On boiling in water for 20 minutes at atmospheric pressure, pieces of this dried product take up 1.6 times their dry weight of water. When fractured at liquid nitrogen temperature in the direction of the fibers, the material is very similar in structure to the product shown in FIGS. 2-5.

EXAMPLE 4

Example 3 is repeated using the same extruded material and equipment, etc. except that the electrodes of the dielectric heater are spaced 13.9 cm apart, the conveyor is operated at 43.2 cm per minute and the power is set at 8.4 kW to the extrudate. Three passes through the dielectric heater are used for each piece being dried. The solids content of the dielectrically dried product is 50%. The product is then cut into pieces which are then dried in an air oven at 90° C for 4 hours. This dry product has a moisture of less than 1%. After boiling in water for 20 minutes at atmospheric pressure, pieces of this product take up 1.6 times their dry weight of water.

What is claimed is:

1. A process comprising dewatering a fermenter effluent to form a mycelial fungal mass which contains from 15 to 40 weight percent solids, dielectrically heating said mass for from 5 to 180 seconds during which period the solids content thereof is increased by from about 8 to about 40 weight percent as based on total dewatered composition whereby a product containing from 30 to 70 weight percent solids is produced.

2. The process of claim 1 wherein the product is further dried to contain less than 10 weight percent water over a period of from about 20 minutes to about 20 hours.

3. The process of claim 1 wherein the fungal mass is mechanically worked to form oriented bundles of mycelia prior to the dielectric heating step.

4. The process of claim 3 wherein the fungal mass has been extruded through at least one mesh screen and compacted into at least one strip prior to the dielectric heating to orient the mycelia and the dielectric field is applied substantially at right angles to the orientation of the fibers.

5. The process of claim 4 wherein said dielectric heating lasts for from 30 to 180 seconds.

6. The process of claim 3 wherein the fungal mass has been extruded through a plate containing holes from 0.32 cm to 1.11 cm in diameter to form strips and the dielectric heating lasts for from 5 to 60 seconds.

7. The process of claim 1 wherein the fungal mass contains from about 20 to about 33 weight percent solids.

8. The process of claim 7 wherein the fungal mass is dielectrically heated to produce a product containing from about 40 to about 60 weight percent solids.

9. The process of claim 8 wherein said dielectric heating lasts for from 30 to 180 seconds.

10. The process of claim 9 wherein the product is further dried to contain less than 10 weight percent water over a period of from about 20 minutes to about 20 hours.

11. The process of claim 10 wherein the fungal mass has been extruded through at least one mesh screen and compacted into at least one strip prior to the dielectric heating to orient the mycelia and the dielectric field is applied at from about 45° to substantially at right angles to the orientation of the mycelia.

12. The process of claim 1 wherein the fungal mass has been thermally pre-treated to reduce the nucleic acid content.

13. A process comprising dewatering a fermenter effluent to form a mycelial fungal mass which contains from 15 to 40 weight percent solids, reducing the turgor of the mycelia until said mycelia become limp, mechanically working said mycelia to form an elongated texturized strip containing oriented mycelia, passing said elongated texturized strip through a dielectric field wherein the residence time of any part of the elongated texturized strip in said dielectric field is from about 30 to about 300 seconds during which period the solids content thereof is increased from 8 to 40 weight percent as based on total dewatered composition whereby a product containing from 30 to 70 weight percent solids is produced.

14. The process of claim 13 wherein the product is further dried to contain less than 10 weight percent water over a period of from about 20 minutes to about 20 hours.

15. The process of claim 14 wherein the dielectric field is applied at right angles to the orientation of the mycelia.

16. The process of claim 15 wherein the dewatered fungal mass contains from about 20 to about 33 weight percent solids.

17. The process of claim 16 wherein the dielectrically dried product contains from about 40 to about 60 weight percent solids.

18. A process comprising dewatering a fermenter effluent to form a mycelial fungal mass which contains from 15 to 40 weight percent solids, reducing the turgor of the mycelia until said mycelia become limp, forming a shaped article from said limp mycelia, applying a dielectric field to said shaped article at a rate such that said shaped article remains within 20 percent of its original volume while the solids content thereof is increased from 8 to 40 weight percent as based on the total dewatered composition whereby a product containing from 30 to 70 weight percent solids is produced, and further drying the article at a slower rate to contain less than 10 weight percent water over a period of from about 20 minutes to about 20 hours.

19. The process of claim 18 wherein the dewatered fungal mass contains from about 20 to about 33 weight percent solids.

20. The process of claim 19 wherein the dielectrically dried article contains from about 40 to about 60 weight percent solids.

21. A process comprising dewatering a fermenter effluent to form a mycelial fungal mass which contains from 15 to 40 weight percent solids, reducing the turgor of the mycelia until said mycelia became limp, mechanically working said mycelia to form an elongated texturized strip from about 0.2 cm to about 15 cm in thickness containing oriented mycelia, passing said elongated texturized strip through a dielectric field applied at a rate such that the volume of the elongated texturized strip remains within 20 percent of its original volume while the solids content thereof is increased from 8 to 40 weight percent as based on the total dewatered composition whereby a product containing from 30 to 70 weight percent solids is produced, and further drying the strip at a slower rate to contain less than 10 weight percent water over a period of from about 20 minutes to about 20 hours.

22. The process of claim 21 wherein the dielectric field is applied at right angles to the orientation of the mycelia.

23. The process of claim 22 wherein the dewatered fungal mass contains from about 20 to about 33 weight percent solids.

24. The process of claim 23 wherein the dielectrically dried product contains from about 40 to about 60 weight percent solids.

25. A mycelial fungal mass having a solids content of from 40 to 60 weight percent which upon being dried to less than a 10 weight percent moisture content has an apparent bulk density of from about 0.52 to 0.73 grams per cc and which on boiling in water at atmospheric pressure will absorb from 1 to 5 times its dry weight of water which mass comprises relatively coarse fibers having a diameter of from 0.2 to 1.0 mm and an average length to diameter ratio of greater than 20, interconnected by hyphae having an average length to diameter ratio of from 10 to 1,000 and an average diameter of from 0.004 to 0.01 mm.

26. The mass of claim 25 which will absorb from 1.5 to 3.0 times its dry weight on boiling in water for 20 minutes at atmospheric pressure.

27. The mass of claim 26 wherein the mycelia contain from 45 to 60 weight percent protein.

28. A texturized mycelial fungal mass, containing less than 10 weight percent moisture, which has an apparent bulk density of from about 0.52 to 0.73 grams per cc which on boiling in water for 20 minutes at atmospheric pressure will absorb from 1 to 5 times its weight of water, which mass comprises relatively coarse fibers having a diameter of from 0.2 to 1.0 mm and an average length to diameter ratio of greater than 20, interconnected by hyphae having an average length to diameter ratio of from 10 to 1,000 and an average diameter of from 0.004 to 0.01 mm.

29. The mass of claim 28 which will absorb from 1.5 to 3 times its weight of water on boiling in water at atmospheric pressure for 20 minutes.

30. The mass of claim 29 wherein the mycelia contain from 45 to 60 weight percent protein.

* * * * *